United States Patent [19]

Tsumura et al.

[11] 4,081,472

[45] Mar. 28, 1978

[54] PROCESS FOR PREPARATION OF AROMATIC ISOCYANATES

[75] Inventors: Ryuichirou Tsumura, Yokohama; Usaji Takaki, Kamakura; Takeshi Abe, Tokyo, all of Japan

[73] Assignee: Mitsui Toatsu Chemicals Inc., Tokyo, Japan

[21] Appl. No.: 711,823

[22] Filed: Aug. 5, 1976

[30] Foreign Application Priority Data

Aug. 7, 1975 Japan .................................. 50-96056

[51] Int. Cl.$^2$ .......................................... C07C 118/00
[52] U.S. Cl. ................................................ 260/453 P
[58] Field of Search ..................................... 260/453 P

[56] References Cited

U.S. PATENT DOCUMENTS

| 3,919,279 | 11/1975 | Rosenthal et al. ................ 260/453 P |
| 3,962,302 | 6/1976 | Rosenthal ......................... 260/453 P |

*Primary Examiner*—Dolph H. Torrence

[57] ABSTRACT

A process is described for preparing aromatic isocyanates by contacting an aromatic carbamate of the formula $R(NHCO_2R')n$ at 150°–350° C under reduced pressure with one or more metal or metal compound catalysts dissolved in an inert solvent. In the formula R is a divalent aromatic, R' is a monovalent aliphatic, alicyclic or aromatic with at most 8 carbon atoms and $n$ is 1 or 2. The metal is dissolved in a concentration of at least 1/1000% by weight of the solvent. The vapors of the resulting aromatic isocyanate and alcohol or phenol are fractionally condensed under reduced pressure and the aromatic isocyanate is separately collected.

7 Claims, No Drawings

PROCESS FOR PREPARATION OF AROMATIC ISOCYANATES

BACKGROUND OF THE INVENTION

The present invention relates to a process for the preparation of aromatic isocyanates wherein aromatic carbamates (referred to hereinafter as the carbamates) are pyrolyzed by bringing them into contact with a catalyst dissolved in a solvent inert to isocyanates.

Isocyanates are very useful substances chiefly as starting materials for polyurethanes. In particular, tolylene diisocyanate, methylene-bis-(4-phenyl isocyanate) and naphthylene diisocyanates are now prepared on a large commercial scale.

A current process for preparing these isocyanates, for example, tolylene diisocyanate of the formula:

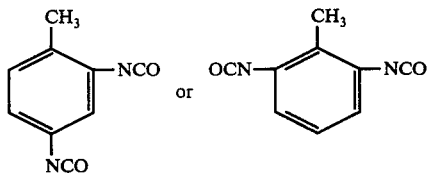

comprises nitrating toluene to form dinitrotoluene, reducing the latter with hydrogen to form the corresponding diamine and then reacting the diamine with phosgene. Namely, the current process comprises complicated and troublesome steps, requring the use of a large amount of highly toxic phosgene and permitting the formation of hydrogen chloride as by-product. In this field, therefore, there is a great demand and research for a new and improved process which requires no phosgene and is simpler and more economical than the above process.

One process which might be considered as a substitute for the current process employing phosgene is a process for preparing isocyanates wherein carbamates are pyrolyzed. Such a process, which relatively easily synthecizes carbamates directly from mitro compounds was developed in recent years. However, the known conventional pyrolysis process is industrially inoperable or economically disadvantageous in respect of yield of isocyanates, reaction rate, materials of construction, control of temperatures and elimination of by-products, and is consequently not practiced as a suitable process for preparing isocyanates.

It has now been found that the above mentioned drawbacks can be overcome when carbamates are subjected to a liquid phase pyrolysis under reduced pressure in the presence of specific catalysts.

The reaction for forming isocyanates by pyrolysis of carbamates may be shown by the following basic equation:

$$RNHCO_2R' \rightarrow RNCO + R'Oh \qquad (1)$$

On thermal dissociation of the carbamate, several undesirable side reactions take place at the same time. These side reactions are: the decarboxylation reaction of the carbamate accompanying the formation of a primary amine $RNH_2$ and an olefin or of a secondary amine $RNHR'$ as by-product; the reaction between the produced isocyanate and the starting carbamate, permitting the formation of an allophanate as by-product; the reaction between the produced isocyanate and an amine formed as by-product permitting the formation of a urea compound as by-product; and the polymerization of the produced isocyanate, permitting the formation of an isocyanurate or a polymer as by product. The thermal dissociation reaction of equation (1) above is reversible and its equilibrium remains with the left-hand side carbamate at normal temperature but is shifted to the right-hand side by heating, whereby the dissociation of the carbamate takes place. In this case, the thermal dissociation temperature varies according to the sort of carbamate and the reaction conditions. Accordingly, it is important for obtaining isocyanates advantageously from carbamates to perform the pyrolysis reaction of equation (1) selectively while inhibiting the above mentioned side and reverse reactions.

The conventional pyrolysis of carbamates is roughly classified into reactions carried out in the vapor phase at a high temperature and reactions carried out in the liquid phase at a relatively low temperature. U.S. Pat. No. 3,734,941 discloses a typical vapor phase process wherein a carbamate is pyrolyzed at 400°–600° C in the presence of a Lewis acid and the resultant vapor is separated by fractional condensation into an isocyanate and an alcohol. According to this process, for example, tolylene diisocyanate is obtained in a yield of 60% by pyrolysis of diethyl tolylene-2,4-dicarbamate of the formula:

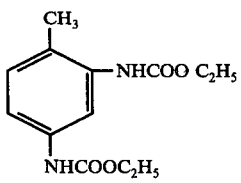

in the presence of ferric chloride. However, this process has the drawbacks of a low yield of the product, decomposition of the catalyst, corrosion of the reaction apparatus at high temperatures, and formation of a considerable amount of a polymer as by-product. German Pat. No. 2,410,505 proposed as an improved vapor phase method a process wherein the residence time of the reactants at 350°–550° C is controlled within 15 seconds. According to this improved process, the yield of isocyanate as high as 93%, although the carbamate has to be supplied in the form of powders to the reaction zone. However, a solid polymer is also formed by this improved process as by-product and is gradually deposited in the reactor and in the condenser during the course of sustained operation, thus making it difficult to conduct a continuous reaction. In addition, a large quantity of heat required for the endothermic pyrolytic reaction has to be supplied to the starting material within a very short period of time. This additional factor causes this improved process to encounter great difficulty in being adopted into practice.

If a liquid phase pyrolysis of the carbamates could be performed at a high reaction rate to afford the end product in a high yield and at a temperature lower than that adopted in the vapor phase methods, elimination of by-products and supply and control of the heat of reaction would become easier and the process as a whole would become very advantageous. According to U.S. Pat. No. 2,409,712, a reaction mixture containing ethoxyethoxyethyl N-laurylcarbamate, synthesized in a yield of 57% by heating laurylamine, urea and ethoxyethoxyethanol at 200° C for 3 hours, is subjected directly to liquid phase pyrolysis conducted at 210°–230° C under reduced pressure of 2 mmHg whereby lauryl isocyanate is isolated in a yield of 75%. This fact shows that a liquid phase pyrolysis of carbamates to isocyanates takes place relatively easily. However, such yield is still too low to be practical. This is due to the reason that in the case of liquid phase pyrolysis of carbamates in the absence of a solvent or in the presence of a solvent containing even such a substance (reactive with isocyanates) as mentioned above, the concentration of the reactants, i.e. the concentration of functional groups such as OH, NCO and $NHCO_2R$ becomes extremely high and the reaction time also increases when compared with the above mentioned vapor phase pyrolysis, so that the various above mentioned side reactions tend to take place and this tendency is more noticeable than the inhibition of the side reactions by lowering the temperature. It is known already to promote thermal dissociation while inhibiting side reactions by diluting the reactants with an inert solvent to lower the concentration of the functional groups.

It has been reported that, as a result of performing the pyrolysis of carbamates in the presence of various amines or fatty acids in an inert solvent such as a hydrocarbon, ether or nitrobenzene, the rate of thermal dissociation is increased as the acidity of alkalinity becomes stronger or as the polarity of the inert solvent becomes higher. [Mukaiyama et al., J. Amer. Chem. Soc. 78, 1946), Bull. Chem. Soc., Japan 33, 1137 (1960)]. It has also been reported that, as result of measuring the thermal dissociation temperatures of various carbamates during the thermal dissociation reaction of various carbamates to tolylene diisocyanates in an inert solvent selected from a paraffin oil and methoxypolyethylene glycol, the thermal dissociation temperature is lower in the case of using the latter inert solvent [G. R. Griffin et al., I & EC Product Research and Development 1, 265 (1962)]. It is thus evident from these reports that a thermally stable solvent with high polarity is desirable as an inert solvent for pryolysis of carbamates.

German patent publication DOS No. 2,421,503 discloses a method of separately recovering isocyanates and alcohols by dissolving carbamates in an inert solvent such as hydrocarbon, ether, ketone or ester and pyrolyzing the carbamates at 175°–350° C under atmospheric or superatmospheric pressure in the presence of a carrier. Carbamates shown in 20 examples of this publication are those capable of forming phenyl isocyanate, tolylene diisocyanate and hexamethylene diisocyanate. The yield of the isocyanate products obtained by separating alcohols formed by thermal dissociation of the carbamates is 22–84% in all examples. The synthesis rate of the isocyanate products is 23–84 g/liter per hour in 6 examples wherein the yields of the isocyanate products are at least 70%. The best yield is obtained in an example wherein tolylene diisocyanate is obtained by pyrolysis of tolylene-2,4-dicarbamate. In this example, the reaction is carried out by continuously supplying n-hexadecane and a solution of the dicarbamate in tetrahydrofuran into a flask charged with n-hexadecane as inert solvent, pyrolyzing the dicarbamate at 250° C under slightly superatmospheric pressure while blowing a large amount of nitrogen as carrier into the flask and recovering the pyrolyzed fraction distilled at 180° C over the top of a fractionating column fitted to the flask after an average resident time of about 20 hours. In a steady stage, the end product, i.e. tolylene diisocyanate is recovered at a yield of 84% and a monocarbamate at a yield of 9%. In this case the synthesis rate of the diisocyanate is about 21 g/liter per hour. The yield obtained in this method is higher than that of the aforementioned U.S. Pat. No. 2,409,712 but is still too low to be practical. In addition, a problem arises in that the reactants are diluted with a solvent so as to decrease the synthesis rate of the isocyanate (the yield of the isocyanate aimed at per unit volume per hour). Accordingly, the isocyanates and the carbamates which easily undergo the above mentioned various side reactions have to be maintained at a high temperature for a long period of time, thus causing a decrease in the yield of the end product. Further, a considerably large capacity is required, thus making the process economically unacceptable. In this liquid phase process, therefore, the yield of the product is not satisfactory and the reaction rate is too small.

The above reference discloses that an acid such as a fatty acid or sulfuric acid or a base such as an amine functions as a catalyst for the thermal dissociation reaction in the liquid phase of carbamates to isocyanates and that the reaction is promoted more smoothly as the acid or base becomes stronger. As such acid or base reacts with the resultant isocyanates, however, the acid or base can no longer be used as catalyst.

Recently a process for preparing isocyanates has been described in U.S. Pat. No. 3,919,278 wherein a mononuclear aromatic carbamate is dissolved in an inert solvent in an amount such that the total concentration of the carbamate and a product obtained by pyrolysis thereof is within a range of about 1–20 mol % and the pyrolysis of the carbamate is carried out at 230–290° C in the presence of an inert carrier used in an amount of at least 3 molar proportion to the carbamate. Another process for preparing isocyanates is described in U.S. Pat. No. 3,919,279 wherein a carbamate is dissolved in an inert solvent and brought into contact at a high temperature with a catalyst composed of a heavy metal (Mo, V, Mn. Fe, Co, Cr, Cu or Ni) or a compound thereof to effect the pyrolysis of the carbamate. The former process (U.S. Pat. No. 3,919,278) is almost identical to that disclosed in the above mentioned German DOS No. 2,421,503, and requires the use of a large amount of a carrier and can hardly be carried out under subatmospheric pressure. The latter process (U.S. Pat. No. 3,919,279) although it uses as a catalyst a specific metal or a compound thereof, is limited to using such catalyst under the reaction conditions in the presence of a carrier under atmospheric or superatmospheric pressure and so cannot be carried out under subatmospheric pressure.

DESCRIPTION OF THE INVENTION

It has now been found surprisingly that although various kinds of metal compounds exhibit a promoting action to the thermal dissociation reaction of carbamates including side reactions, only specific metals, i.e. those belonging to Groups I-B, II-B, III-A, IV-A, IV-B, V-B and VIII of the Periodic Table strongly function catalytically, especially in the dissolved state and their catalytic action does not essentially depend on the form or combination of the starting materials for the catalyst and the combining ingredients.

Based on the above finding, the present inventors have succeeded in solving the problems raised by the liquid phase thermal dissociation reaction of carbamates and have developed a process for preparing isocyanates in highly acceptable yields and at high reaction rates.

According to the process of the present invention and contrary to all prior art, a catalytic pyrolysis reaction can effectively be carried out under subatmospheric pressure in the absence of a carrier without dissolving a carbamate necessarily in an inert solvent. This is a fundamentally different mode of reaction from the above processes and exhibits, as will be illustrated in examples given hereinafter, remarkably high reaction rate, superiority in the cost of starting materials resulting from the use of no carrier and higher yields.

The prime objects of the present invention, therefore, provide the following:

1. A process for the preparation of aromatic isocyanates in a very high yield from the corresponding aromatic carbamates wherein the reaction is carried out under reduced pressure in the presence of specific catalysts.
2. A process for the preparation of aromatic isocyanates in a very high yield wherein aromatic carbamates are pyrolyzed at an extremely high reaction rate under reduced pressure in the presence of specific catalysts.
3. A process for the preparation of aromatic isocyanates of high purity wherein aromatic carbamates are pyrolyzed.
4. A non-corrosive, economical, practical catalyst of long life and having high catalytic activity and selectivity which is useful in the process for the preparation of the aromatic isocyanates wherein aromatic carbamates are subjected to a liquid phase pyrolysis as well as the use of the catalyst.
5. An inert solvent which is stable to heat and to aromatic isocyanates, is capable of dissolving the catalyst and discretely the aromatic carbamates and is useful in the process for the production of the aromatic isocyanates wherein the aromatic carbamates are subjected to a catalytic liquid phase pyrolysis reaction as well as the use of the inert solvent.
6. A process for the preparation of aromatic isocyanates wherein the supply of the heat of the dissociating endothermic reaction of aromatic carbamates and control of the reaction temperature are rendered simple.
7. A process for the preparation of aromatic isocyanates wherein the operation can continuously be carried out while easily separating a small amount of by-products with boiling points higher than those of the aromatic isocyanate.
8. A process for continuously preparing aromatic diisocyanates in a high yield wherein aromatic dicarbamates are pyrolyzed.

Briefly stated, the process of the present invention is carried out by bringing an aromatic carbamate into contact at a temperature of 150°–350° C under reduced pressure with a catalyst dissolved in an inert solvent to effect pyrolysis of the aromatic carbamate, collecting the resultant isocyanate and alcohol in the form of vapors, and thereafter separately condensing both vapor products. In case a diisocyanate is desired as the end product of the process, an isocyanato-carbamate compound in which only one of the dicarbamate groups has been dissociated is produced intermediately. Such intermediate product having a high boiling point is converted into the desired polyisocyanate by immediately fractionating the reaction products and refluxing only the high boiling component back to the reactor or by distilling the desired polyisocyanate from the isocyanate fraction containing all the condensed products other than alcohol components and recycling the still residue to the reactor.

The aromatic carbamates used in the present invention as starting material are represented by the general formula: $R(NHCO_2R')n$ In the formula, R is a monovalent or divalent aromatic group with at most 32 carbon atoms. R may contain an isocyanato group and a monovalent or divalent substituent not reactive therewith, R' is a monovalent aliphatic, alicyclic or aromatic hydrocarbon group with at most 8 carbon atoms and may contain an isocyanato group or a monovalent substituent not reactive therewith. And $n$ is an integer of 1 or 2 and corresponds to the valency of the substituent R.

Illustrative of the substituent R are aryl groups such as phenyl, tolyl, xylyl, naphthyl, biphenylyl, anthryl, phenanthryl, terphenyl, naphthacenyl and pentacenyl groups and divalent groups formed by removing one hydrogen atom from these aromatic groups. These aromatic groups may contain an isocyanato group; a substituent not reactive therewith such as an alkyl group, a halogen atom, nitro group, cyano group, an alkoxy group, an acyl group, an acyloxy group or an acylamido group; or a divalent substituent of similar nature such as a methylene group, an ether group, a thioether group, a carbonyl group or a carboxyl group. Examples of the substituent R' include aliphatic groups such as methyl, ethyl, propyl, butyl, hexyl, octyl and methoxyethyl groups; alicyclic groups such as a cyclohexyl group; and aromatic groups such as phenyl and tolyl groups.

Typical examples of the carbamates utilizable in the present invention include methyl phenylcarbamate, ethyl phenylcarbamate, propyl phenylcarbamate, butyl phenylcarbamate, octyl phenylcarbamate, ethyl naphtyl-1-carbamate, ethyl anthryl-1-carbamate, ethyl anthryl-9-carbamate, diethyl anthrylene-9,10 dicarbamate, ethyl p-biphenylylcarbamate, diethyl m-phenylenedicarbamate, diethyl naphthylene-1,5-dicarbamate, methyl p-tolylcarbamate, ethyl p-trifluoromethylphenylcarbamate, isopropyl m-chlorophenylcarbamate, ethyl 2-methyl-5-nitrophenylcarbamate, ethyl 4-methyl-3-nitrophenylcarbamate, ethyl 4-methyl-3-isocyanatophenylcarbamate, methylene-bis-(phenyl-4-ethylcarbamate), dimethyl tolylene-2,4-dicarbamate, diethyl tolylene-2,4-dicarbamate, diethyl tolylene-2,6-dicarbamate, diisopropyl tolylene-2,4-dicarbamate, dibutyl tolylene-2,4-dicarbamate, diphenyl tolylene-2,4-dicarbamate, diphenyl tolylene-2,6-dicarbamate, di(ethoxyethyl) tolylene-2,4-dicarbamate, diethyl 4-chlorophenylene-1,3-dicarbamate, methyl p-butoxyphenylcarbamate, ethyl p-acetylphenylcarbamate, ethyl o-nitrophenylcarbamate and isopropyl m-trifluoromethylphenylcarbamate. Of these carbamates compounds, the most practical examples are the tolylenedicarbamates, naphthylenedicarbamates and methylene-bis-(phenylcarbamate).

In the present invention, the pyrolysis reaction is carried out by bringing the carbamate into contact at a temperature of 150°–350° C under reduced pressure with one or more compounds of metals belonging to Groups I-B, II-B, III-A, IV-A, IV-B, V-B and VIII of the Periodic Table. These metal compounds should be dissolved in an inert solvent to have a metal concentration of at least 0.001% by weight at the reaction temperature, any insoluble moiety of the metal compounds being allowed to co-exist. The main catalytic action to pyrolysis of the carbamates is displayed by the dissolved metal component itself and not by the combined form thereof or of its combined components. Accordingly, no particular limitation exists in the combined components for the metal utilizable as the catalyst and in the method for using the catalyst. Any method capable of dissolving the metal component in the inert solvent so as to have the desired concentration at the reaction temperature may be employed.

Metals belonging to Groups I-B, II-B, III-A, IV-A, IV-B, V-B and VIII of the Periodic Table or organic or inorganic compounds thereof may be used as the catalyst utilizable in the present invention. Preferably, compounds of copper, zinc, aluminum, tin, titanium, vanadium, iron, cobalt and nickel are employed. Examples of the metal compounds used as catalyst include metal salts with aliphatic, alicyclic and aromatic carboxylic acids such as formic acid, acetic acid, lauric acid, stearic acid, oxalic acid, azelaic acid, naphthenic acid, tetrahydrophthalic acid, benzoic acid, phthalic acid and pyromellitic acid; metal alcoholates with aliphatic and alicyclic alcohols such as methanol, ethanol, propanol, butanol, octanol, dodecyl alcohol, benzyl alcohol, ethylene glycol, propylene glycol, polyethylene glycol, glycerol, pentaerythritol and cyclohexyl alcohol as well as the corresponding metal thioalcoholates; metal phenolates with monohydric or polyhydric phenol derivatives such as phenol, cresol, nonylphenol, catechol and hydroquinone as well as the corresponding metal thiophenolates; metal salts with sulfonic acids such as methanesulfonic acid, ethanesulfonic acid, dodecanesulfonic acid, cyclohexanesulfonic acid, benzenesulfonic acid, toluenesulfonic acid and dodecylbenzenesulfonic acid; metal chelates with chelating agents, for example, $\beta$-diketones such as acetylacetone and benzoylacetone, ketoesters such as ethyl acetoacetate and ethyl benzoacetate, hydroxyaldehydes such as salicylaldehyde and 2-hydroxy-1-naphthaldehyde, amino acids such as glycin, alanine, aspartic acid, glutamic acid, serine, tyrosine and iminodiacetic acid, and hydroxy acids such as glycolic acid, lactic acid and salicylic acid; metal carbamates with carbamates defined as the starting material for the present invention as well as the corresponding metal thiocarbamates and dithiocarbamates; metal salts with compounds having anionic ligands such as hydroxyl group, nitric acid group, phosphoric acid group, boric acid group and cyanato group; and metal complexes of the above mentioned various metal salts with ligands having a non-covalent electron pair such as amines, phosphines, phosphites, nitriles and amides. These metal compounds are used as such to catalize the reaction. In case a metal salt derived from the anionic ligand has a poor solubility in an inert solvent, such metal salt may be added to the reaction system exceptionally together with a carboxylic acid, an alcohol, a phenol, a sulfonic acid or a chelating agent so as to increase the concentration of the metal in the inert solvent to a given value. In the case of metal powders or metal oxides, these may be dissolved in the inert solvent in a manner similar to the aforementioned.

Preferred examples of catalysts include copper naphthenate, zinc naphthenate, zinc acetate, zinc oxalate, zinc benzoate, zinc hexylate, zinc dithiocatecholate, zinc dodecylbenzenesulfonate, zinc acetylacetonate, zinc N,N-ethylphenyldithiocarbamate, zinc hydroxide, zinc oxide and naphthenic acid, aluminum benzoate, aluminum isobutylate, aluminum salicylaldehydate, tin acetate, tin octanoate, dibutyl tin dilaurate, titanium oxalate, titanium naphthenate, titanium phenolate, vanadium naphthenate, vanadium acetylacetonate, iron naphthenate, iron acetoacetate, cobalt naphthenate, bis-triphenylphosphine cobalt nitrate, nickel naphthenate and bis-pyridine nickel nitrate.

The preferred amount of the metal compound used as catalyst may be within a range of 0.01–10% by weight based on the inert solvent used for the reaction. A most preferred amount of the metal compound varies according to the sort of catalyst and the mode of its use, but is usually within a range of 0.05–1% by weight.

The inert solvent utilizable for the reaction of the present invention is a high boiling inert solvent which has a boiling point of at least 200° C under normal pressure and is not reactive with the isocyanate but capable of dissolving the metal compound used as the catalyst. For example, the inert solvent may be selected from hydrocarbons, ethers, thioethers, ketones, thioketones, sulfones, esters, organosilane compounds and mixtures of these compounds. The solvent should dissolve the metal compound so as to afford a metal concentration of at least 0.001% by weight at the reaction temperature. The effect achieved by the use of the solvent is that the dissolved metal component of the catalyst is brought into effective and even contact in the liquid or at the surface with the carbamate in dissolved, suspended or emulsified dilute state whereby a selective reaction is promptly initiated and promoted. Thus, this solvent need not necessarily dissolve the carbamate but desirably may dissolve it. The solvent also functions as a heat medium serving to supply heat to the reaction system and to make the reaction temperature uniform. Furthermore, the solvent serves to remove from the reactor a small amount of by-products having boiling points higher than the boiling point of the isocyanate. Useful solvents have a boiling point at least 50° C higher than the boiling point of the isocyanate, are stable at the reaction temperature, are capable of dissolving both catalyst and carbamates and are easily available at a low cost.

Preferred examples of hydrocarbons as the inert solvent include aliphatic hydrocarbons such as the higher alkanes, dodecane, hexadecane, octadecane, and liquid paraffin, the corresponding alkenes, petroleum fractions of paraffin series such as those usually employed as lubricating oils or cutting oils; alicyclic hydrocarbons such as petroleum fractions of the naphthene series; aromatic hydrocarbons such as dodecylbenzene, dibutylbenzene, methylnaphthalene, phenylnaphthalene, benzylnaphthalene, biphenyl, diphenylmethane, terphenyl and aromatic petroleum fractions usually employed as rubber-treating oils; and substituted aromatic compounds having no reactivity with the isocyanate such as chloronaphthalene, nitrobiphenyl and cyanonaphthalene. Other preferred inert solvents are, for example, ethers and thioethers such as diphenyl ether, methyl naphthyl ether, diphenyl thioether and the like aromatic ethers and thioethers; ketones and thioketones such as benzophenone, phenyl tolyl ketone, phenyl benzyl ketone, phenyl naphthyl ketone and the like aromatic ketones or thioketones; sulfones such as diphenyl sulfone and the like aromatic sulfones; esters such as animal and vegetable oils, dibutyl phthalate, dioctyl phthalate, phenyl benzoate and the like aliphatic and aromatic esters; organosilane compounds such as conventional silicone oils. Among these solvents, high boiling petroleum fractions of paraffin series, naphthene series or aromatic series are especially practical.

Although no limitation exists in the amount of the solvent used, the amount by weight is usually within a range of 0.1–100 times the amount of the carbamate, the optimal value depending on the mode of reaction. In a continuous reaction, the solvent in an amount by weight of 0.1–10 times the supplied amount of the starting carbamate is recycled to the reactor. Although a small amount of by-products having boiling points higher than those of the desired isocyanate and the alcohol are produced in the course of pyrolysis of the carbamate, a continuous pyrolytic reaction can be carried out over a long period of time with a minimum amount of the solvent without any trouble by withdrawing the by-products from the reactor together with the solvent, separating the by-products from the solvent and recycling the solvent alone to the reactor.

In the process of the present invention, the reaction temperature is within a range from 150° to 350° C. The reaction temperature should be above the temperature at which dissociation of the carbamate usually begins (about 150° C). However, above 350° C, the reaction proceeds too rapidly thus giving rise to side reactions very pronouncedly and the reaction becomes less economical in view of the increase in heating cost. An optimum temperature has to be determined according to the sort of starting carbamate used, but a temperature within a range from 200° to 300° C is generally desirable. Although it is necessary to supply an amount of heat to satisfy the needs of the endothermic reaction and of the latent heat of evaporation of the products, this can easily be supplied by the solvent itself, which also functions as a heat transfer medium.

The reaction is carried out under reduced pressure. A proper pressure is selected in connection with the temperature according to the sort of the carbamate used, so as to meet the requirement for recovering the product as vapor. Usually, an absolute pressure within a range of 10–400 mmHg is desirable. In special reactions, however, wherein an isocyanate with a high boiling point is to be obtained or the thermal degradation of the product is to be prevented, the reaction may be carried out under an absolute pressure within a range of 1–10 mmHg in a reactor such as a film evaporator.

The reaction time is within a range from a few seconds to several hours. The reaction time varies chiefly according to the sort of carbamate, the type and amount of catalyst, the reaction temperature, the reaction pressure and the mode of the reaction adopted, but it can significantly be shortened by the catalytic effect achieved by the present invention as compared with the case of using no catalyst. In Examples 3–6, for instance, the rates of the formation of isocyanates are increased by about 3 times by the use of a catalyst.

The process of the present invention may be carried out also batchwise, but is desirably carried out continuously in a completely mixing type or an extrusion flow type reactor. In a continuous process, for example, the carbamate in a powdery or molten form or as a mixture with the inert solvent is supplied to a reactor which has previously been charged with a given catalyst and the inert solvent and has optionally been preheated to a given temperature under a given pressure. The isocyanate and the alcohol produced by the pyrolytic reaction are separately condensed by taking advantage of the difference in their boiling points.

The present invention affords a very high yield of the product without the aid of any carrier, contrary to the processes of the above mentioned German DOS No. 2,421,503 and U.S. Pat. Nos. 3,919,278 and 3,919,279.

With the present invention, a small amount of non-volatile by-products is formed in the reactor. However, such by-products can be readily removed from the reactor together with the reaction liquid when this and the catalyst dissolved therein are continuously withdrawn from the reactor. The reaction liquid from which the by-products have been removed is then pre-heated and recycled to the reactor as inert solvent containing the catalyst. Although the life of the catalyst is sufficiently long, the small loss of catalyst during the prolonged operation necessitates an occasional addition of fresh catalyst to the reactor or to the recycling liquid.

When polyisocyanate is prepared, an isocyanatocarbamate is formed as an intermediate product. As the boiling point of this intermediate is higher than that of the polyisocyanate, the preparation of the polyisocyanate is carried out by either a process wherein the intermediate product is not distilled for the reactor or by a process wherein the intermediate product is distilled from the reactor together with the polyisocyanate and alcohol, separated therefrom by distillation and recycled to the reactor.

No special material of construction is required for the apparatus for carrying out the process of the present invention. Commonly used stainless steel or ordinary steel can be used with impunity.

According to the process of this invention, an isocyanate fraction of high purity (95% or higher) and an alcohol fraction can be obtained in very high yields (about 95% or more) as pyrolytic products of the carbamate at a very satisfactory reaction rate by the effect of a very small amount of catalyst. Pure isocyanate may of course be obtained by distillation of the isocyanate fraction with any conventional method.

EXAMPLES

The present invention will now be illustrated in more detail by way of examples. The following examples show by way of illustration but not in a limitative sense the results of the pyrolysis of the commercially most useful carbamate, diethyl tolylene-2,4-dicarbamate [referred to hereinafter simply as 2,4-DCT(Et)] according to the two typical modes of reaction showing the effects of the catalyst of this invention. A first mode is directed to a refluxing method wherein the intermediate product is refluxed to the reactor; the second mode is directed to a non-refluxing method wherein the whole reaction product in the vapor state is distillated from the reactor. Refluxing method: The equipment included a 200 ml round-bottomed flask equipped with an inlet for feeding the carbamate, a distillation tower of 25 mm I.D. filled with MacMahon packings to a height of 100 mm. A stirrer or alternatively a capillary for introduction of nitrogen into a catalyst solution for promoting diffusion of the molten carbamate into the catalyst solution or contact between them instead of stirring the catalyst solution and a thermocouple for adjusting the reaction temperature. After charging the flask with given amounts of a catalyst and a solvent, a carbamate was molten in a vat for fusing the starting material and supplied at a constant flow rate through a needle valve into the flask maintained at a given temperature and pressure. When the capillary was used, the flow rate of the nitrogen was only that necessary to maintain good contact between the catalyst solution and the molten carbamate. The amount of nitrogen necessary for this purpose was only about 1 ml/minutes, contrary to the above mentioned U.S. Pat. Nos. 3,919,278 and 3,919,279, where the flow rate of nitrogen as carrier is at least 100 ml/min. and actually at least 1 liter/min. Thus, it is evident that the very small amount of nitrogen used in the present invention does not function as a carrier.

When a stirrer was used, nitrogen was not at all used. The isocyanate as end product and the alcohol produced by the pyrolytic reaction were separated in the distillation tower from the intermediate product (e.g., a monoisocyanatomonocarbamate) and from the high-boiling by-products and were taken out in vapor form from the top of the tower. The vapor product was first cooled with a water-cooled condenser connected to the top of the tower to collect the condensed isocyanate and then cooled in a dry ice trap where the alcohol was condensed and collected. After a continuous supply of carbamate for 1.5–3 hours under given reaction conditions, the distillation rates of the isocyanate and the alcohol for the supplied carbamate were calculated from the weights of the isocyanate and the alcohol collected. The compositions of both products were measured by NCO analysis, gas chromatography and high speed liquid chromatography and thereafter the yields of NCO groups, isocyanate and alcohol from the starting carbamate were calculated. By weighing the contents of the flask after completion of the pyrolytic reaction, the rate of formation of non-distilled by-products having high boiling points as a non-distilled fraction was calculated on the basis of the carbamate fed and then a material balance was calculated. Prior to the pyrolytic reaction, the reaction solvent was pre-heated to a temperature 50° C higher than the reaction temperature under a pressure lower than the actual reaction pressure in order to remove any moisture and other contaminants having low boiling points. Non-refluxing method: This method contemplates the immediate removal from the reaction system of all of the vaporized products formed during the pyrolytic reaction. While in the refluxing method, yield and synthesis rate of the desired isocyanate are influenced by the distillation tower incidental to the reactor, in the non-refluxing method a comparison is possible of results of the reaction under uniform conditions and is thus suitable for judging the effect of the catalyst.

This method was carried out in the quite same manner as the fluxing method except that the distillation tower was detached from the reaction flask and a fractional condenser was directly attached to the reaction flask.

EXAMPLE 1

According to the refluxing method, the flask was charged with 0.152 g of zinc naphthenate as catalyst and 50 g of a petroleum fraction of paraffin series (NURAYN 165 produced by Exxon Corp.) as solvent. To the catalyst solution was added, while maintaining the flask under a reduced pressure of 20 mmHg and at 250° C by heating with a mantle heater, 2,4-DCT (Et) (in molten state and maintained at 150° C) at a rate of 0.39 g/min. for 91 minutes. The flow rate of nitrogen introduced through the capillary was about 1 ml/min. corresponding in total to only 3 mol % of the supplied carbamate. After a few minutes from the initiation of supply of the carbamate, the products were distilled at a constant rate at 122° C. The distilled product was subjected to fractional condensation at 30° C to collect the isocyanate fraction and then passed through a dry ice trap where ethanol formed by the pyrolytic reaction was condensed and collected. Using 35.4 g of dicarbamate, 21.9 g (61.9% in the distillation rate) of isocyanate fraction and 12.1 g (34.2% in the distillation rate) of ethanol fraction were obtained. By analysis, the isocyanate fraction contained 47.3% by weight of NCO groups and was composed of 96% by weight of desired tolylene-2,4-diisocyanate (referred to hereinafter simply as 2,4-TDI) and 4.0% by weight of ethyl tolylene-2,4-monoisocyanatomonocarbamate of the formula:

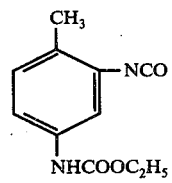

[referred to hereinafter as 2,4-ICT(Et)] as an intermediate product, while the ethanol fraction contained 96% by weight of ethanol. The production rate of non-distilled by-products was 2.3% by weight including what remained in the tower. The recovered products constituted 98.4% based on the starting 2,4-DCT(Et).

The yields of the products were calculated as follows:
NCO groups: 92%
2,4-TDI: 91%
2,4-ICT (Et): 3.1%
ethanol: 95%

A similar pyrolytic reaction was carried out using the recovered reaction solution containing the catalyst from which by-products had been removed. The results of this reaction were nearly the same as above and no deterioration of the catalyst was observed. A second and similar pyrolytic reaction was carried out using a 700 rpm stirrer instead of the nitrogen flow. Also in this case, results of the reaction were nearly the same as above, thus proving that no carrier gas is necessary.

REFERENCE EXAMPLE 1

For purpose of comparison, a pyrolytic reaction was carried out in the same manner as described in Example 1 except that no catalyst was used. As a result of the reaction, the distillation rates of the isocyanate and ethanol fractions were 53.0% and 31.8%, respectively, and the production rate of the non-distilled by-products was 12.9%. The isocyanate fraction contained 45.2% of NCO groups an was composed of 89% TDI and 11% ICT while the ethanol fraction contained 98% ethanol. The yields were found to be:
NCO groups: 76%
TDI: 72%
ICT: 7.3%
ethanol: 90%

A comparison of the above results with that of Example 1 revealed that although the pyrolysis of the starting carbamate took place nearly to the same extent in both cases, the yields of NCO groups and TDI in the case of Reference Example 1 were very low but the production rate of non-distilled by-products was about 6 times greater than in Example 1. A result of this comparison indicates that in the pyrolytic reaction carried out in the absence of the catalyst, the selectivity to TDI is considerably decreased. Thus, a comparison between Example 1 and Reference Example 1 teaches that the catalyst has a remarkable effect for selectively promoting pyrolytic conversion of carbamate groups into NCO groups and inhibiting occurrence of side reactions.

EXAMPLES 2–4 AND REFERENCE EXAMPLE 2

For the purpose of illustrating the effect of the catalyst more explicitly, the pyrolytic reaction of carbamates was carried out in the presence and in the absence of catalyst according to the non-refluxing method. The reactor was charged with 0.10 g of catalyst and 50 g of results of the experiments are shown in Table 2 below.

Table 2

Catalytic pyrolysis of diethyl tolylene -2,4-dicarbamate according to the refluxing method

| Ex. No. | Catalyst | Distillation rate (%) TDI Fraction | Distillation rate (%) Ethanol Fraction | Production rate of non-distilled material (%) | Composition of TDI fraction (%) NCO Group | TDI | ICT | Yield (%) NCO Group | TDI | ICT | Ethanol* |
|---|---|---|---|---|---|---|---|---|---|---|---|
| 5 | Aluminum sec-butylate | 63.3 | 34.0 | 2.9 | 46.6 | 95 | 4.2 | 94 | 92 | 3 | 97 |
| 6 | Zinc N,N-ethylphenyl-dithiocarbamate | 65.4 | 34.2 | 0.4 | 46.8 | 95 | 5.0 | 97 | 95 | 4 | 98 |
| 7 | Zinc acetate | 63.9 | 34.0 | 0.3 | 47.2 | 96 | 3.7 | 95 | 94 | 3 | 95 |
| 8 | Zinc stearate | 60.9 | 32.6 | 3.5 | 46.8 | 95 | 5.4 | 90 | 88 | 4 | 92 |
| 9 | Zinc benzoate | 63.5 | 33.4 | 1.3 | 46.9 | 93 | 6.5 | 94 | 91 | 5 | 97 |
| 10 | Zinc p-methyldithio-cathecolate | 62.7 | 33.5 | 0.8 | 46.3 | 95 | 3.2 | 92 | 91 | 2 | 96 |
| 11 | Zinc acetylacetonate | 65.2 | 33.4 | 0.2 | 44.1 | 88 | 8.4 | 91 | 88 | 7 | 94 |
| 12 | Tin acetate | 60.0 | 31.6 | 3.9 | 46.8 | 95 | 4.7 | 89 | 87 | 3 | 90 |
| 13 | Copper naphthenate | 62.4 | 33.2 | 5.5 | 47.1 | 96 | 2.7 | 93 | 92 | 2 | 93 |
| 14 | Titanium oxalate | 64.1 | 31.3 | 3.2 | 44.5 | 90 | 6.4 | 91 | 88 | 5 | 90 |
| 15 | Vanadium acetyl-acetonate | 63.5 | 33.4 | 3.0 | 46.7 | 96 | 1.8 | 94 | 93 | 1 | 95 |
| 16 | Iron naphthenate | 62.4 | 32.9 | 1.1 | 46.0 | 92 | 8.0 | 91 | 88 | 6 | 90 |
| 17 | Cobalt naphthenate | 63.2 | 33.4 | 2.7 | 46.4 | 96 | 0.8 | 93 | 93 | 1 | 94 |
| 18 | Nickel naphthenate | 60.7 | 33.1 | 3.1 | 46.2 | 94 | 4.6 | 89 | 87 | 3 | 92 |

*The yield of ethanol was calculated from the amount of ethanol contained in the ethanol fraction.

a petroleum fraction of the naphthene series (JWS 8510B, Exxon Corp.) as solvent. To the catalyst solution was added, while maintaining the reactor under a reduced pressure of 20 mmHg at 250° C, 2,4-DCT(Et) in molten state and maintained at 150° C at a rate of 0.5 g/min. for about 2 hours and the pyrolytic reaction was carried out continuously. A result of the experiments is shown in Table 1.

The results tabulated in Table 2 show that TDI having a purity of at least 95% was obtained in high yields (nearly 90-95%). A test piece of SUS 27 steel was placed in the reaction flask during the reaction but no corrosion was observed thereon after the 20-hour test.

Using a tower of 30 mm I.D. filled with MacMahon packings to a height of 300 mm, the TDI fraction thus obtained containing 95% TDI and 5% ICT was contin- Table 1

Pyrolysis of diethyl tolylene-2,4-dicarbamate according to the non-refluxing method

| Example No. | Catalyst | Distillation rate (%) TDI fraction | Distillation rate (%) Ethanol fraction | Composition of TDI fraction (%) NCO groups | TDI | ICT | Yield (%) NCO groups | TDI | ICT | Ethanol** | Synthesis rate of TDI g/liter/hr |
|---|---|---|---|---|---|---|---|---|---|---|---|
| 2 | Aluminum sec-butylate | 64.8 | 29.0 | 35.9 | 63 | 29 | 74 | 62 | 23 | 83 | 220 |
| 3 | Zinc N,N-ethyl-phenyl-dithio-carbamate | 69.5 | 28.9 | 35.1 | 61 | 30 | 77 | 65 | 25 | 81 | 230 |
| 4 | Zinc dodecyl-benzene-sulfonate | 65.3 | 26.7 | 36.3 | 62 | 34 | 75 | 62 | 27 | 74 | 220 |
| Ref 2* | None | 66.7 | 21.5 | 23.2 | 21 | 68 | 49 | 22 | 55 | 55 | 75 |

*Reference Example 2
**The yield of ethanol was calculated from the amount of ethanol contained in the ethanol fraction.

Almost similar results were obtained when a 700 rpm stirrer was used instead of the small nitrogen flow.

When the catalyst was used, the TDI content in the TDI fraction, the yield of TDI and the synthesis rate of TDI in each Example were about 3 times as much as those in Reference Example 2 wherein no catalyst was employed, thus indicating the remarkable technical effect of the catalyst, especially for promoting selectivity in the reaction.

EXAMPLES 5-18

Using various kinds of catalyst, the pyrolytic reaction was carried out in the same manner as described in Example 1 in which the refluxing method was employed, except that the amount of catalyst used was 0.1 g, the feed rate of diethyl tolylene-2,4-dicarbamate was 0.4-0.5 g/min., the rotational speed of the stirrer was about 700 rpm and the reaction time was 1.5-3 hours. The catalyst was used so that the concentration of the metal contained therein was within the range of 0.01-0.1% by weight based on the solvent used. The uously distilled whereby a pure TDI fraction having a purity of 99.8% was obtained at a distillation rate of 98%.

EXAMPLE 19

As a result of the pyrolytic reaction carried out in the same manner as described in Example 1 except that 0.1 g of zinc hydroxide and 0.35 g of naththenic acid were used as catalyst, the distillation rates of TDI and ethanol fractions were 61.5% and 34.4%, respectively, and the TDI fraction was composed of 46.6% NCO groups, 96% TDI and 3.0% of ICT. The yield of NCO groups was 91%, that of TDI 90%, ICT 2% and ethanol 99%.

EXAMPLE 20

A pyrolytic reaction was carried out in the same manner as described in Example 1 except that a mixture of diethyl tolylene-2,4-dicarbamate and diethyl tolylene 2,6-dicarbamate in a mixing ratio of 80:20 parts by weight was used as starting material in place of diethyl tolylene-2,4-dicarbamate alone. As a result of this pyrolytic reaction, the distillation rates of TDI and ethanol fractions were 63.0% and 33.4%, respectively, and the TDI fraction was composed of 46.0% NCO groups, 95% TDI and 2.3% ICT. The yield of NCO groups was 92%, that of TDI 91%, ICT 2% and ethanol 97%.

It is understood that the preceding representative examples may be varied within the scope of the present specification, both as to reactants and reaction conditions, by one skilled in the art to achieve essentially the same results.

As many apparently widely different embodiments of this invention may be made without departing from the spirit and scope thereof, it is to be understood that this invention is not limited to the specific embodiments thereof except as defined in the appended claims.

What is claimed is:

1. A process for the preparation of aromatic isocyanates, comprising the steps of: providing an aromatic carbamate of the general formula:

$$R(NHCO_2R')n$$

wherein R is selected from monovalent and divalent aromatic groups with at most 32 carbon atoms, R' is selected from monovalent aliphatic, alicyclic and aromatic groups with at most 8 carbon atoms, and $n$ is an integer selected from 1 and 2; contacting said aromatic carbamate at a temperature of 150°–350° C and subatmospheric pressure with an solution of at least one compound selected from the group consisting of, carboxylates; alcoholates; phenolates; sulfonates; chelates with a chelating agent selected from β-diketones, ketoesters, hydroxyaldehydes, amino acids and hydroxyacids; carbamates; thio-and dithiocarbamates; hydroxides; nitrates; phosphates; borates; complexes with a neutral ligand selected from amines, phosphines, phosphites, nitriles and amides; and oxides of at least one metal selected from the group consisting of copper, zinc, aluminum, tin, titanium, vanadium, iron, cobalt and nickel as catalyst, said catalyst being dissolved in an inert solvent having a boiling point of at least 200° C in a metal concentration of at least 0.001% by weight based on said solvent, to effect the pyrolysis of said aromatic carbamate and to obtain vapors of aromatic isocyanate and by-product vapors; thereafter subjecting all of said vapors to fractional condensation under subatmospheric pressure to collect said aromatic isocyanate separately from said by-product vapors.

2. The process according to claim 1 wherein the reaction pressure is at most 400 mmHg absolute and the reaction temperature is 200°–300° C.

3. The process according to claim 2 wherein said inert solvent is a high boiling petroleum fraction selected from the paraffin series, the naphthene series and the aromatic series.

4. The process according to claim 1 wherein said aromatic carbamate is an alkyl ester selected from alkyl esters of tolylene-2,4-dicarbamic acid and alkyl esters of tolylene-2,6-dicarbamic acid.

5. The process according to claim 4 wherein a monoisocyanatomonocarbamate is formed as an intermediate product of reaction and is recycled to the reactor.

6. The process according to claim 2 wherein the metal part of said catalyst is at least one metal selected from zinc, aluminum, tin, and titanium.

7. The process according to claim 4 wherein the metal part of said catalyst is aluminum.

* * * * *

UNITED STATES PATENT AND TRADEMARK OFFICE
CERTIFICATE OF CORRECTION

PATENT NO. : 4,081,472
DATED : March 28, 1978
INVENTOR(S) : Ryuichirou Tsumura et al.

It is certified that error appears in the above-identified patent and that said Letters Patent are hereby corrected as shown below:

Page 1 [75] Inventors: change "Ryuichirou" to -- Ryuichiro --

Column 4, line 58, column 6, line 58 and column 7, line 5, each occurrance, change "III-A" to -- III-B --

Column 4, line 59, column 6, line 58 and column 7, line 6, each occurrance, change "V-B" to -- V-A --

Signed and Sealed this

Twenty-ninth Day of August 1978

[SEAL]

Attest:

RUTH C. MASON
Attesting Officer

DONALD W. BANNER
Commissioner of Patents and Trademarks